United States Patent [19]

Pring

[11] Patent Number: 4,974,423
[45] Date of Patent: Dec. 4, 1990

[54] CONTAINER FOR TRANSPORT OF FROZEN MATERIALS SUCH AS BIOLOGICAL SAMPLES

[76] Inventor: John B. Pring, 17 Riverside, Folly Island, Hertfort, Herts SG13, England

[21] Appl. No.: 439,349

[22] Filed: Nov. 20, 1989

[30] Foreign Application Priority Data

Nov. 22, 1988 [GB] United Kingdom ............... 8827283

[51] Int. Cl.⁵ .................................................. F25D 3/08
[52] U.S. Cl. ..................................... 62/371; 435/284; 435/296
[58] Field of Search ............... 435/296, 284, 291, 298; 62/237, 250, 337, 371, 457.1, 529; 165/918, 61, 46

[56] References Cited

U.S. PATENT DOCUMENTS

| | | | |
|---|---|---|---|
| 1,979,222 | 10/1934 | Goodwin | 165/918 X |
| 4,022,199 | 1/1977 | Jacobs | 165/918 X |
| 4,377,077 | 3/1983 | Granlund | 62/457.1 |
| 4,509,587 | 4/1985 | Clark et al. | 62/457.1 |
| 4,537,044 | 8/1985 | Putnam | 62/371 |
| 4,738,364 | 4/1988 | Yeager | 62/457.1 |
| 4,825,666 | 5/1989 | Sara, III | 62/457.1 |

FOREIGN PATENT DOCUMENTS 167936 3/1951 Austria ................... 62/371

Primary Examiner—Larry Jones
Attorney, Agent, or Firm—Ostrolenk, Faber, Gerb & Soffen

[57] ABSTRACT

A portable container for the transport of frozen samples, for example biological samples. The container has two compartments, one to contain the sample and the other to contain a portable refrigerant such as dry ice. Readouts are included to check for when the dry ice needs replenishment, and also to check on whether the container has at any time risen to a dangerous temperature, e.g. −5° C.

6 Claims, 1 Drawing Sheet

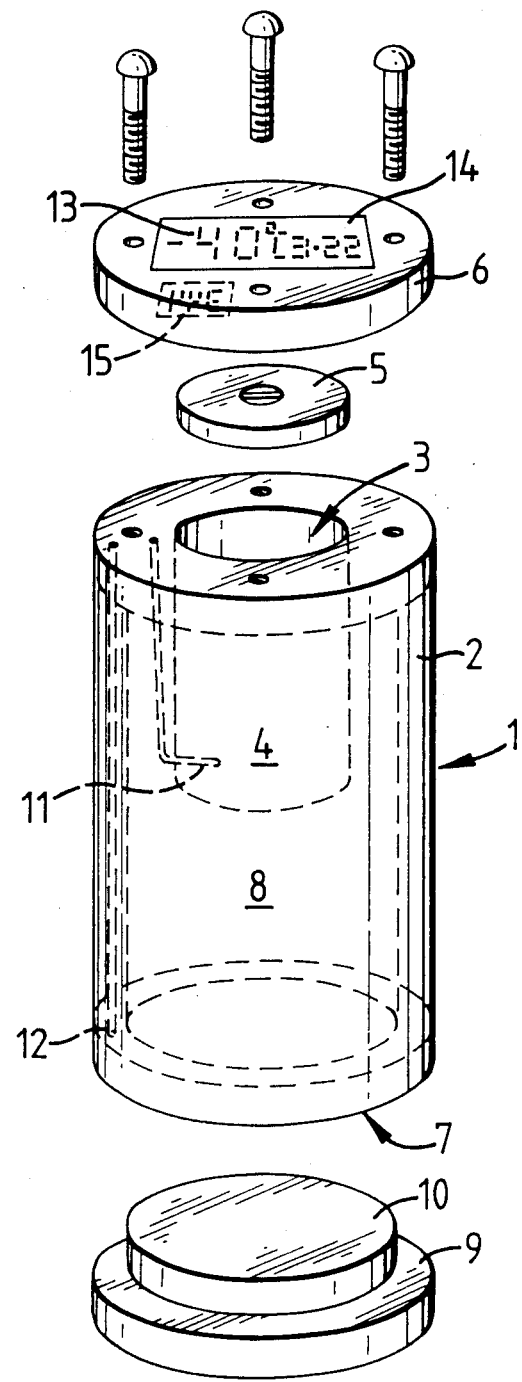

CONTAINER FOR TRANSPORT OF FROZEN MATERIALS SUCH AS BIOLOGICAL SAMPLES

The present invention relates to the transport of frozen materials for example frozen biological samples.

In general if frozen biological samples are to be transported it is important that if the samples are to remain viable, the temperature should remain below −20° C. Similar conditions arise in relation to frozen foodstuffs, although not necessarily to the same degree.

This has been achieved in the past by packing the materials in a container with dry ice, however this gives rise to the problem that contamination from the dry ice may be transferred to the product, and there may be risk that the product has risen in temperature during use and then being refrozen. In particular if transport takes place over a period of time it is important to take steps to ensure the product has not risen in temperature during that time and then be refrozen by some third party. For example if intermediate handling of the product by third parties arises, it is difficult to know whether or not this has happened.

The present invention is concerned with these problems.

Accordingly the present invention provides an insulated container for transport of frozen material, for example biological samples, having a first compartment to receive the frozen material to be transported and closed by a first closure, and a second compartment to receive and hold a quantity of portable refrigerant in proximity to said first compartment and closed by a second closure, the two closures being spaced apart so as to minimize the possibility of cross contamination between the two compartments.

Preferably the two closures are on opposite sides of the container so that, for example, one is in the top and the other is in the base.

The term portable refrigerant is used here to refer to materials which can have heat extracted therefrom and can then be used for cooling purposes. Materials in solid form such as water ice or dry ice or liquid nitrogen are examples. Bags containing a liquid eutectic material such as is used in cool boxes for camping and the like also come within this term. Solid $CO_2$ is particularly suitable for use in the invention.

The container in accordance with the invention may be provided with a temperature sensing means, for example a thermistor in the first compartment connected to an electrical read out on the outside, and preferably this should be able to record the thermal history of the frozen material during storage in the container. This feature enables any occurrence of unsafe rise in temperature to be recorded.

It is also preferable that the second closure has a tamper proof seal so that refrigerant cannot be replenished during transport without the owner or recipient being aware of that fact. Any form of seal which gives evidence of the fact that the closure has been opened is suitable, provided it is compatible with the frozen material to be transported.

An embodiment of the invention will now be described by way of example with respect to the accompanying single figure which shows a perspective view of the container and its two closures.

The container comprises a main body 1 of right circular cylindrical shape which is double walled to include insulation cavities 2, and has two openings extending into its interior.

The first of these openings, 3, extends in from the top and opens into a first compartment 4 which is intended for reception of the frozen material to be transported (e.g. biological samples).

The first compartment 4 is closed by closure 5, which has a recessed handle to permit removal, and is a plug fit within the opening 3. An insulated electronics package 6 is bolted in position above the closure 5.

The second opening 7 opens into the interior of the container from underneath, to provide access to a second compartment 8 for reception of the refrigerant material such as dry ice. The second compartment 8 is closed by a closure 9 which on its upper face includes an insulating plug 10 which is a snug fit within the opening 7.

The electronics package 6 is thermally insulated to ensure reliability, comprises three readouts, and is connected via pressure connections between the package 6 and the body of the container 1 and thence via conduit to a temperature sensor 11 within the compartment 4 and a pressure switch 12 which is arranged to detect opening of the lower closure 9.

Two of the readouts are located on top of the electronics package 6 (see Figure) and consist of a temperature readout 13 which directly reads the temperature within compartment 4 via the sensor 11, and a timer 14 which indicates the time which has elapsed since charging the compartment 8 with dry ice, i.e. since last removal of the closure 9 and deactivation of pressure switch 12. The third readout 15 (shown dotted) is a second timer and this is located on the underside of the electronics package 6, so as not to be visible to the outside world. This timer is arranged to start counting elapsed time if and when the temperature sensor rises to a danger level e.g −5° C.

The electronic circuitry for measuring and indicating temperature measured by the sensor 11, and for counting and indicating the elapsed time in the two timers is quite straightforward, would be readily apparent to the skilled man in the art and therefore is not described.

In use, for transport of biological samples, the container will be inverted, and the closure 9 will be removed to enable the second container to be filled with a quantity of solid $CO_2$ to serve as a refrigerant. This sets the top timer 14 at zero.

After the closure 9 has been replaced it will then be sealed with a seal (not shown) which has to broken for further access to be obtained to the compartment. The container is then turned back to its upright position. The first closure can then be removed for loading of the frozen material into the first compartment after which the first closure 5 will be replaced and secured in position. The container will then be shipped in its upright position with the indicators uppermost. An advantage of the circular cross-section at this stage is that the container will stand out from other rectangular packages, and its indicators will then be less likely to be missed during routine checks.

It will be recognized by virtue of the two closures requiring the container to be turned over during loading, that the likelihood of any cross contamination between the refrigerant material and the sample to be loaded in the first compartment is minimized.

During transport, the temperature and elapsed time indicators on top of the container will show whether the contents are safe for further transport or whether the $CO_2$ needs replenishment. For example if the temperature shows $-40°$ C. and 3.22 hours and only has a short journey, it will be safe. If at this stage the container is to go on an eight hour journey and it is known that the $CO_2$ would last only a further three hours, the handlers will know that the container is not safe for that journey. For such a journey therefore, the bottom closure 9 would need to be opened in order to replenish the $CO_2$, and in so doing the elapsed time indicator would be reset to zero.

As a further precaution the second timer is set to start counting elapsed time if and when the temperature rises above $-5°$ C. Thus if on receipt of the product at the end of its journey, and the electronics package is unbolted for removal of the contents, the timer 15 shows 3.44 hours, this shows that the product reached a dangerous temperature 3.44 hours ago. This enables the location during the journey at which the product became dangerous to be pinpointed, and by comparison of the two timers the time during which the product was at a dangerous temperature to be worked out. Thus, if the top timer 14 shows 3.22 hours and the underside timer 15 shows 3.44 hours, that means that the product was at or above $-5°$ C. for 0.22 hours.

What is claimed:

1. A portable insulated container for transport of material, for example biological samples, said container comprising
   a first compartment for receiving material to be transported and a first closure closing said first compartment,
   a second compartment for receiving and holding a quantity of portable refrigerant in proximity to said first compartment and a second closure closing said second compartment, said first and second closures being remotely spaced from one another to minimize the possibility of cross-contamination between said first and second compartments,
   a first externally visible readout, a temperature sensor located within said first compartment and connected to said first externally visible readout,
   a second hidden readout arranged for measurement of the time elapsed from when the temperature in the first compartment has risen to a given preset temperature, and
   a timer having a third externally visible readout and connected for measurement of the time elapsed from sealing of said second closure, thereby to indicate when said second compartment needs replenishing with portable refrigerant.

2. A portable insulated container according to claim 1 in which the container has opposing sides and the two closures are on the opposing sides of the container.

3. A portable insulated container according to claim 1 in which the second closure has a tamper proof seal.

4. A portable insulated container according to claim 1 which is cylindrical and of circular cross section.

5. A portable insulated container according to claim 1 comprising a thermally insulated electronics pack arranged to be attached to the top of the first container and having the externally visible readouts on its upper surface and the hidden readout on its under surface.

6. A portable insulated container according to claim 2, wherein said container has a top and a base and said two closures on opposing sides of said container are at said top and said base of said container, respectively.

* * * * *